(12) United States Patent
Hartley

(10) Patent No.: US 7,846,665 B2
(45) Date of Patent: *Dec. 7, 2010

(54) NUCLEIC ACID MARKER LADDER FOR ESTIMATING MASS

(75) Inventor: James Hartley, Frederick, MD (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/237,587

(22) Filed: Sep. 25, 2008

(65) Prior Publication Data

US 2009/0111112 A1 Apr. 30, 2009

Related U.S. Application Data

(63) Continuation of application No. 11/534,575, filed on Sep. 22, 2006, now Pat. No. 7,455,974, which is a continuation of application No. 10/410,176, filed on Apr. 10, 2003, now Pat. No. 7,132,520, which is a continuation of application No. 09/666,890, filed on Sep. 20, 2000, now Pat. No. 6,680,378, which is a continuation of application No. 09/114,911, filed on Jul. 14, 1998, now abandoned, which is a continuation of application No. 08/893,523, filed on Jul. 11, 1997, now Pat. No. 5,834,201, which is a continuation of application No. 08/142,124, filed on Oct. 28, 1993, now abandoned.

(51) Int. Cl.
C12Q 1/68 (2006.01)
C07H 21/00 (2006.01)

(52) U.S. Cl. .......................... 435/6; 536/22.1

(58) Field of Classification Search ............... 435/6; 536/22.1
See application file for complete search history.

(56) References Cited

U.S. PATENT DOCUMENTS

| | | | |
|---|---|---|---|
| 4,403,036 A | 9/1983 | Hartley et al. | |
| 4,582,788 A | 4/1986 | Erlich | |
| 4,683,194 A | 7/1987 | Saiki et al. | |
| 4,683,195 A | 7/1987 | Mullis et al. | |
| 4,683,202 A | 7/1987 | Mullis | |
| 5,030,566 A | 7/1991 | Son et al. | |
| 5,108,179 A | 4/1992 | Myers | |
| 5,137,814 A | 8/1992 | Rashtchian et al. | |
| 5,316,908 A | 5/1994 | Carlson et al. | |
| 5,714,326 A | 2/1998 | Dawson | |
| 5,834,201 A * | 11/1998 | Hartley | 435/6 |
| 5,840,575 A | 11/1998 | Hyman | |
| 6,680,378 B1 * | 1/2004 | Hartley | 536/22.1 |
| 6,924,098 B2 * | 8/2005 | Hu et al. | 435/6 |
| 7,132,520 B2 * | 11/2006 | Hartley | 536/22.1 |
| 7,455,974 B2 * | 11/2008 | Hartley | 435/6 |

FOREIGN PATENT DOCUMENTS

| | | |
|---|---|---|
| EP | 466404 | 1/1992 |
| EP | 0725821 | 7/1998 |
| WO | WO91/18095 | 11/1991 |
| WO | WO93/14224 | 7/1993 |
| WO | WO95/011971 | 5/1995 |

OTHER PUBLICATIONS

Non-Final Office Action received for U.S. Appl. No. 11/534,575 mailed on Feb. 8, 2008.
Notice of Allowance received for U.S. Appl. No. 11/534,575 mailed on Sep. 18, 2008.
Response to Non-Final Office Action received for U.S. Appl. No. 11/534,575 filed on Aug. 7, 2008.
Bethesda Research Laboratories, "Nucleic Acid Molecular Weight Standards", *Life Technologies, Inc.*, 1985, pp. 58-59.
Boehringer, Mannheim Biochemical, "Alphabetical Index", *Boehringer Mannheim*, 1992, p. A-10.
Boehringer, Mannheim Biochemical, "DNA Sizing Made Simple", *BM Biochemica*, vol. 9(6), Nov. 1992, pp. 1 and 7.
Boehringer, Mannheim Biochemical, "Molecular Weight Markers", *Boehringer Mannheim*, 1993, p. 63.
Gelfi, Cecilia et al., "DNA sequencing in HydroLink matrices: Extension of reading ability to >600 nucleotides", *Electrophoresis*, vol. 11, No. 8, 1990, pp. 595-600.
GIBCO/BRL Catalog & Reference, 1991/1992, pp. 316-317.
GIBCO/BRL Catalog & Reference, 1992, pp. 316-317 and 322.
Hartley, James L., et al., "Cloning Multiple Copies of a DNA Segment", *Gene* vol. 13, 1981, pp. 347-353.
Invitrogen, "BRL Catalog & Reference Guide", Life Technologies, Inc., 1989, pp. 78-84 and 238.
Invitrogen, "Nucleic Acid Molecular Size Standards", *GIBCO BRL GIBCO/BRL Catalog*, 1992, pp. 315-325.
Maniatis, et al., "Appendix A: Biochemical Techniques. Quantitation of DNA and RNA in Molecular Cloning" A Laboratory Manual, *Cold Spring Harbor Laboratory Press*, 1982, pp. 468-469.
Mathew, M. K., et al., "High-Resolution Separation and Accurate Size Determination in Pulsed-Field Gel Electrophoresis of DNA. 1. DNA size standards and the effect of agarose and temperature", *Biochem.*, vol. 27, 1988, pp. 9204-9210.
Sambrook, Joseph, et al., "Ch: 6.15- Staining DNA in Agarose Gels", *Molecular Cloning: A Laboratory Manual, 2nd Ed.*, Cold Springs Harbor Laboratory Press, 1989, pp. 6.15-6.19.
Sharp, Philip A., et al., "Detection of Two Restriction Endonuclease Activities in Haemophilus Parainfluenzae Using Analytical Agarose-Ethidium Bromide Electrophoresis", *Biochemistry* vol. 12, No. 16, 1973, pp. 3055-3063.
The Stratagene Catalog, 1988, p. 39.

* cited by examiner

*Primary Examiner*—Ethan Whisenant

(57) ABSTRACT

The invention relates to a nucleic acid marker ladder which is a restriction endonuclease digest, wherein a nucleic acid restriction endonuclease digest is a collection of nucleic acid fragments resulting from complete digestion of one or more nucleic acids by one or more restriction endonucleases; the restriction endonuclease digest contains at least 3 fragments; and the size of the fragments in base pairs is a multiple of an integer, wherein the integer is 10 or more.

8 Claims, 2 Drawing Sheets

NUCLEIC ACID MARKER LADDER FOR ESTIMATING MASS

CROSS REFERENCE TO RELATED APPLICATIONS

This is a continuation of U.S. application Ser. No. 11/534,575 filed on Sep. 22, 2006, now allowed, which is a continuation of U.S. application Ser. No. 10/410,176, filed Apr. 10, 2003, now U.S. Pat. No. 7,132,520, which is a continuation of U.S. application Ser. No. 09/666,890, filed Sep. 20, 2000, now U.S. Pat. No. 6,680,378, which is a continuation of U.S. application Ser. No. 09/114,911, filed Jul. 14, 1998 (abandoned), which is a continuation of U.S. application Ser. No. 08/893,523, filed Jul. 11, 1997, now U.S. Pat. No. 5,834,201, which is a continuation of U.S. application Ser. No. 08/142,124, filed Oct. 28, 1993, abandoned. The disclosures of the above-referenced applications are incorporated herein by reference in their entireties.

FIELD OF THE INVENTION

The present invention is in the field of molecular biology and specifically relates to the technique of gel electrophoresis of nucleic acid fragments.

BACKGROUND OF THE INVENTION

Gel electrophoresis of nucleic acid is a well known technique in molecular biology. Nucleic acid molecules are separated on the basis of size (length or molecular weight), and conformation (linear vs. nicked circles vs. covalently closed circles). For a given conformation, electrophoretic mobility is inversely related to size.

Conventional agarose gel electrophoresis is commonly used for the separation of nucleic acid fragments within a practical resolution limit of 50 kbp (Cantor, C. R. and Schimmel, P. R. (1980) *Biophysical Chemistry*, Vol. III, pp. 1012-1036, Freeman, San Francisco; and Maniatis, T. et al. (1982) *Molecular Cloning: A Laboratory Manual*, Cold Spring Harbor Laboratory Press, Cold Spring Harbor, N.Y.). A method called pulsed field gel electrophoresis (PFGE) has been developed to provide separation of DNA molecules up to 2 Mbp (Schwartz, D. C. et al. (1983) *Cold Spring Harbor Symp. Quant. Biol.* 47:189-195.; and Schwartz, D. C. and Cantor, C. R. (1984) *Cell* 37:67-75).

A number of mixtures of nucleic acid fragments ("ladders") are commercially available that can be used as markers for determining or estimating the sizes of nucleic acid molecules during gel electrophoresis. One type of ladder is constructed by digesting plasmids or bacteriophage with one or more restriction enzymes. The size of the marker fragments will depend upon the natural location of the restriction enzyme site within the molecule to be digested and will produce a quasi-random size distribution. For example digestion of bacteriophage λ (lambda) with HindIII produces fragments of 23,130, 9,416, 6557, 4361, 2322, 2027, 564, and 125 base pairs (bp) (See Cat. No. 5612SA, Life Technologies, Inc. 1992 catalogue, Gaithersburg, Md., p. 318).

Alternatively, a ladder may comprise fragments which vary linearly with molecular weight, i.e. adjacent bands may differ by about 1000 base pairs (e.g "1 Kb DNA Ladder", See Cat. No. 5615SA, Life Technologies, Inc. 1992 catalogue, Gaithersburg, Md., p. 323), 100 base pairs (e.g "100 bp DNA Ladder", See Cat. No. 5628SA, Life Technologies, Inc. 1992 catalogue, Gaithersburg, Md., p. 322), or 123 bp (e.g "123 bp DNA Ladder", See Cat. No. 5613SA, Life Technologies, Inc. 1992 catalogue, Gaithersburg, Md., p. 323). Some ladders have been constructed and sold that are logarithmically spaced ("GenePrint™", cat. no. DG1911, Promega, Madison, Wis.).

Nucleic acid is visualized in agarose gels following electrophoresis by staining with the florescent dye ethidium bromide (Sharp et al. (1973) *Biochemistry* 12:3055). Ethidium bromide contains a planar group that intercalates between nucleic acid bases. The fixed position of this planar group and its close proximity to the nucleic acid bases cause the ethidium bromide bound to the nucleic acid to display an increased fluorescent yield compared to that of ethidium bromide in free solution (See Sambrook et al. (1989) Molecular Cloning, 2nd edition, Cold Spring Harbor Laboratory Press, Cold Spring Harbor, N.Y., page 6.15). The molecular mass of a nucleic acid fragment can be determined following agarose gel electrophoresis and ethidium bromide staining by comparing the intensity of the fluorescence of a fragment of unknown molecular mass with the intensity of a similarly sized fragment of known molecular mass.

SUMMARY OF THE INVENTION

In general, the present invention provides a nucleic acid marker ladder. More specifically, the present invention provides a nucleic acid marker ladder consisting essentially of a restriction endonuclease digest wherein (a) the nucleic acid restriction endonuclease digest is a collection of nucleic acid fragments resulting from the complete digestion of one or more nucleic acids by one or more restriction endonucleases;

(b) the restriction endonuclease digest contains at least 3 fragments; and (c) the size of the fragments in base pairs is a multiple of an integer, wherein the integer is 10 or more.

The present invention also provides a nucleic acid marker kit comprising a carrier means having in close confinement therein at least one container means where a first container means contains the above-described nucleic acid marker ladder.

The present invention also provides a method of preparing a nucleic acid marker ladder comprising:

(a) generating at least two polymerase chain reaction (PCR) products wherein each product is generated from a template comprising a restriction endonuclease site and a primer comprising the restriction endonuclease site in the template;

(b) joining the PCR products to produce one or more nucleic acid molecules; and (c) completely digesting the nucleic acid molecules with at least one restriction endonuclease wherein a nucleic acid marker ladder is produced wherein the ladder contains at least 3 fragments and the size of the fragments in base pairs is a multiple of an integer, wherein the integer is 10 or more.

Further objects and advantages of the present invention will be clear from the description that follows.

DETAILED DESCRIPTION OF THE INVENTION

Figure 1:
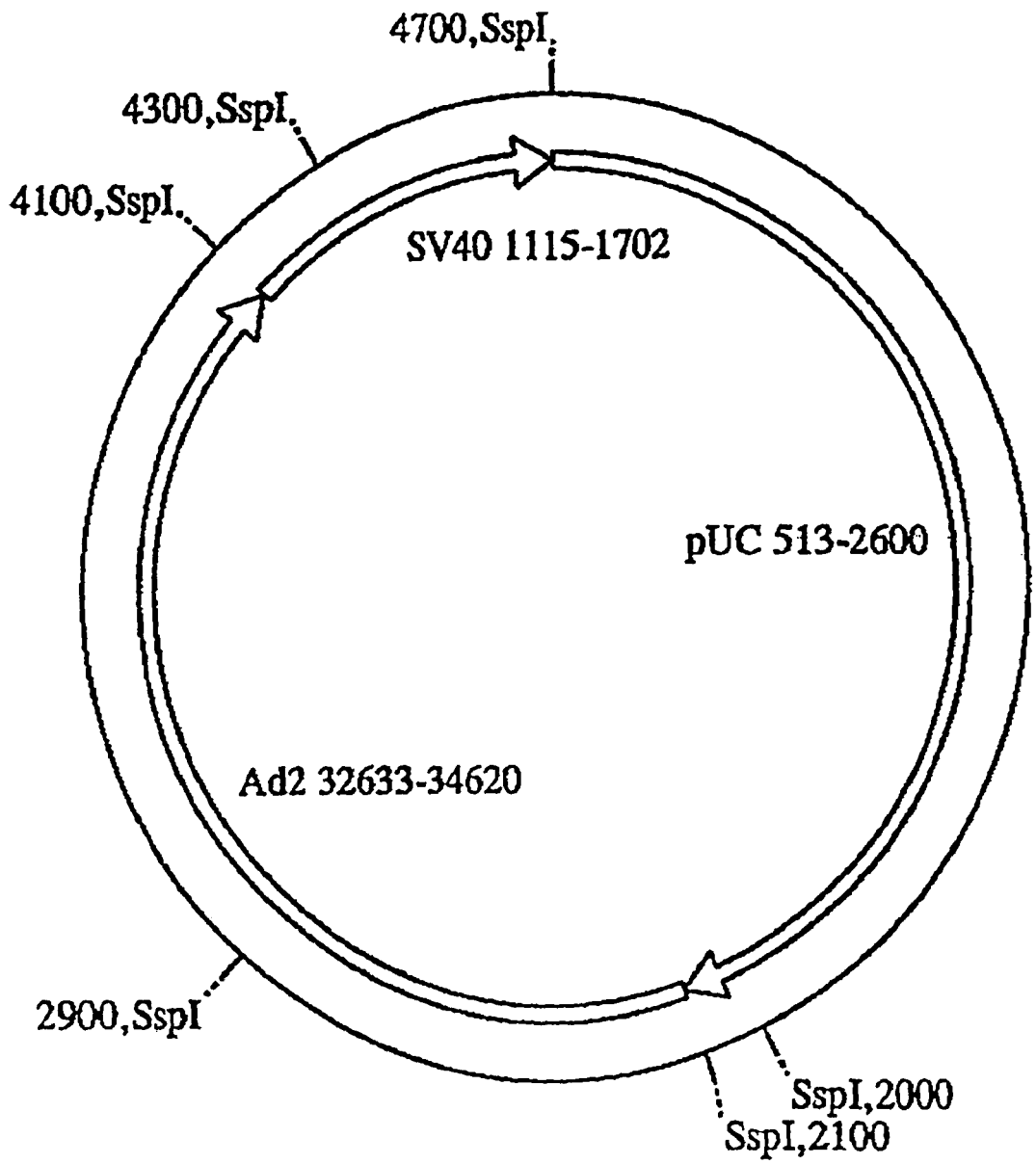
FIG. 1. A plasmid map of pML1 (Mass Ladder).
Figure 2:
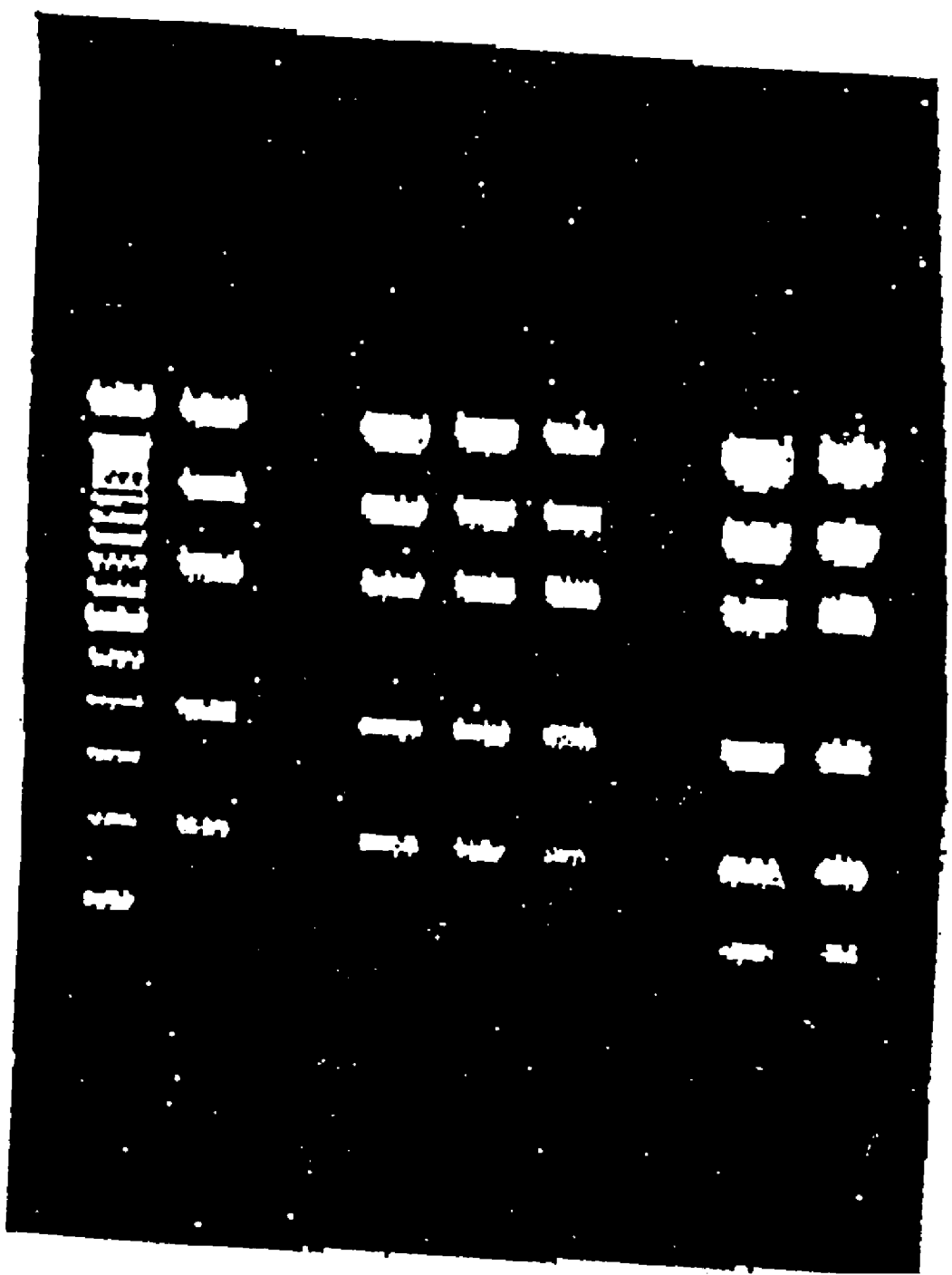
FIG. 2. Restriction enzyme digest of pML1. Lane 1. 100 bp ladder (See Cat. No. 5628SA, Life Technologies, Inc. 1992 catalogue, Gaithersburg, Md., p. 322); Lanes 2, 4-6, 8-9. SspI digest of pML1.

The present invention relates to a nucleic acid marker ladder.

In one embodiment, the present invention relates to a nucleic acid marker ladder consisting essentially of a restriction endonuclease digest, wherein (a) the nucleic acid restriction endonuclease digest is a collection of nucleic acid fragments resulting from the complete digestion of one or more nucleic acids by one or more restriction endonucleases;

(b) the restriction endonuclease digest contains at least 3 fragments; and (c) the size of the fragments in base pairs is a multiple of an integer, wherein the integer is 10 or more. In one preferred embodiment the integer is 10. In another preferred embodiment, the integer is 25. In yet another preferred embodiment, the integer is 50. In a further embodiment, the integer is 100. In another preferred embodiment, the collection of nucleic acid fragments results from digestion of a nucleic acid by one restriction endonuclease. In a further preferred embodiment, the nucleic acid is DNA. One skilled in the art would recognize that the size of the fragments can be approximately a multiple of an integer. For example, the fragment's size can be 101, 201, 301, and 401 bp.

In another embodiment, the present invention relates to a nucleic acid marker kit comprising a carrier means having in close confinement/therein at least one container means where a first container means contains the above-described nucleic acid marker ladder.

A restriction endonuclease (also restriction enzyme) is an enzyme that has the capacity to recognize a specific base sequence (usually 4, 5, or 6 base pairs in length) in a DNA molecule, and to cleave the DNA molecule where this sequence appears. For example, EcoRI recognizes the base sequence GAATTC/CTTAAG.

The DNA molecules produced by digestion with a restriction endonuclease are referred to as restriction fragments. Any given genome, plasmid or phage may be digested by a particular restriction endonuclease into a discrete set of restriction fragments.

The most commonly used analytical method (though not the only one) for fractionating double-stranded DNA molecules on the basis of size is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel. The DNA fragments fractionated by agarose gel electrophoresis can be visualized directly by a staining procedure if the number of fragments included in the pattern is small. Preferably, the nucleic acid-containing agarose gel is stained with ethidium bromide.

As will be understood by those of skill in the art, the nucleic acid molecules used to form the marker ladder are preferably any linear or circular DNA which is cleavable by a restriction enzyme. For example, the nucleic acid may be chromosomes, plasmids, cosmids or viral nucleic acid. Preferably, the nucleic acid molecules are plasmid or viral molecules and derivatives thereof. The nucleic acid present in the plasmid or viral molecule may include exogenous nucleic acid which has been joined to produce the plasmid or viral molecule. In one preferred embodiment, the nucleic acid is DNA.

In another embodiment, the present invention relates to a method of preparing a nucleic acid marker ladder comprising:

(a) generating at least two polymerase chain reaction (PCR) products wherein each product is generated from a template comprising a restriction endonuclease site and a primer comprising the restriction endonuclease site in the template;

(b) joining the PCR products to produce one or more nucleic acid molecules; and (c) completely digesting the nucleic acid molecules with at least one restriction endonuclease wherein a nucleic acid marker ladder is produced wherein the ladder contains at least 3 fragments and the size of the fragments in base pairs is a multiple of an integer, wherein the integer is 10 or more.

To construct a nucleic acid molecule which when digested with a restriction endonuclease produces the marker ladder of the present invention, the number of fragments in the restriction endonuclease digest and the desired size of the fragments are selected. In one preferred embodiment, the restriction endonuclease digest contains at least three fragments. In another preferred embodiment, the restriction endonuclease digest contains 3, 4, 6, 8 or 10 fragments. In a further preferred embodiment, the restriction endonuclease digest contains 6 fragments.

The size of the fragments in base pairs is preferably selected to be a multiple of an integer, wherein the integer is 10 or more. In one preferred embodiment, the integer is 10, 25, 50, or 100. In another preferred embodiment, the integer is 100.

Preferably, one of the fragments contains an origin of replication (for example, ori) such that the nucleic acid molecule may autonomously replicate within a cell. It is also preferable that one of the fragments contains a selectable or screenable marker. The origin of replication and the marker may be present on the same fragment. Transformants containing this DNA fragment may be cultured and selected with a selection agent corresponding to the selectable marker.

The nucleic acid molecule is preferably constructed from polymerase chain reaction (PCR) products. The polymerase chain reaction provides a method for selectively increasing the concentration of a nucleic acid molecule having a particular sequence even when that molecule has not been previously purified and is present only as a single copy in a particular sample. The method can be used to amplify single or double stranded nucleic acid. Reviews of the polymerase chain reaction are provided by Mullis, K. B., *Cold Spring Harbor Symp. Quant. Biol.* 51:263-273 (1986); Saiki, R. K., et al., *Bio/Technology* 3:1007-1012 (1985); Mullis, K. B., et al., *Methods in Enzymology* 155:350 (1987); Mullis, K., et al., U.S. Pat. No. 4,683,202; Erhlich, H., U.S. Pat. No. 4,582,788; and Saiki, R., et al., U.S. Pat. No. 4,683,194.

In one preferred embodiment, a PCR product has the desired restriction endonuclease site internally. In another preferred embodiment, a PCR product has the desired restriction endonuclease site at the right and/or left end of the PCR product. In a further preferred embodiment, the PCR product has the desired restriction endonuclease site internally and at the right or left end of the PCR product.

The PCR product is preferably generated from a naturally occurring template. The template is preferably plasmid, phage, or plant, animal, or bacterial genomic DNA. The template preferably has an internal restriction endonuclease site. The desired restriction endonuclease site at the right or left end of the PCR product is preferably generated by a restriction endonuclease site in the PCR primer.

The spacing of the PCR priming sites and the naturally occurring restriction sites is preferably arranged so that when the PCR products are joined together, the nucleic acid molecule so formed when harvested from *E. coli* can be cut with the desired restriction endonuclease to produce the digest of the present invention.

For example, if a ladder of 6 fragments is preferred, three PCR products may be joined together. Product 1 would preferably contain joinable ends A and C, wherein C contains the desired restriction endonuclease site. Product 1 would also preferably contain the desired restriction endonuclease site (B) internally.

Product 1 A B C

Product 2 would preferably contain joinable ends D and F, wherein F contains the desired restriction endonuclease site. Product 2 would also preferably contain the desired restriction endonuclease site (E) internally.

Product 2 D E F

Product 3 would preferably contain joinable ends G and I, wherein I contains the desired restriction endonuclease site. Product 3 would also to preferably contain the desired restriction endonuclease site (H) internally.

Product 3 G H I.

The primer ends are constructed such that C is joinable to D, F is joinable to G, and I is joinable to A. The primer ends A, C, D, F, G, and I are variable and depend upon the desired size of the fragments present in the digest.

The PCR products can be joined together using ligase (preferably, *E. coli* DNA ligase, Cat. No. 8052SA, Life Technologies, Inc., Gaithersburg, Md.) to produce a nucleic acid molecule. The molecule is then digested with at least one restriction endonuclease wherein a nucleic acid marker ladder is produced wherein the ladder contains at least 3 fragments and the size of the fragments in base pairs is a multiple of an integer, wherein the integer is 10 or more. Preferably, one restriction endonuclease is used. The six fragments produced from digestion of the above-described molecule are B-C, C-E, E-F, F-H, H-I, and I-B.

In the examples that follow, DNA from three sources was joined together to form a nucleic acid which when cleaved with a restriction enzyme produces a marker ladder of 6 fragments wherein the fragments are multiples of 100.

The present invention is useful as a standard to be used during electrophoresis. A marker ladder wherein the size of the fragments is a multiple of an integer (preferably an integer of 10 or more) is extremely convenient and easy to use since one skilled in the art can quickly calculate the size of an unknown nucleic acid fragment.

However, the marker ladder of the present invention not only allows one to size a nucleic acid but also to determine the mass of the nucleic acid. The molecular mass of a nucleic acid fragment can be determined following agarose gel electrophoresis and ethidium bromide staining by comparing the intensity of the florescence of a fragment of unknown molecular mass with the intensity of a similarly sized fragment of known molecular mass. The molecular mass is easily determined because all of the fragments derive from a single nucleic acid molecule.

The present invention is described in further detail in the following non-limiting examples.

EXAMPLE 1

Construction of an SspI Marker Ladder

A marker ladder was constructed from three PCR products. Each PCR product has an Ssp I at its right end, and an internal Ssp I site (naturally occurring in the DNA template). The spacing of the priming sites and the naturally occurring restriction sites was arranged so that when the three PCR fragments were annealed together (uracil bases in the 5' ends of the primers, treated with uracil DNA glycosylase (Life Technologies, Inc., Gaithersburg, Md.); 3' ends anneal; U.S. Pat. Nos. 5,137,814 and 5,229,283) to form a circular molecule, the plasmid so formed when harvested from *E. coli* can be cut (to completion) into six Ssp I fragments, all of which are multiples of 100 bp.

Three polymerase chain reactions were performed with each of the following three sets of primers:

```
A Spacer pUC coord. 525
pUC left:
5' [auc uga ccu cau] [aat tta] [cgg aag cat aaa
gtg taa agc ct] 3'

B' Ssp I pUC coord. 2600
pUC right: 5' [agu cac agc uau] [aat att] [gga aat
gtg cgc gga acc cc] 3'

B Spacer Ad2 coord. 32645
Adeno2 left:
5' [aua gcu gug acu] [aat tta] [cta gtg aat cca cag
aaa cta gc] 3'

C' Ssp I Ad2 coord. 34620
Adeno2 right:
5' [aca ucu gga cuu] [aat att] [aga cat att gat
aag gtg gcg ag] 3'

C Spacer SV40 coord. 1127
SV40 Left:
5' [aag ucc aga ugu] [aat tta] [ggg aca gtt tgg
caa ggt ttt ta] 3'

A' Ssp I SV40 coord. 1702
SV40 right:
5' [aug agg uca gau] [aat att] [taa gcc ttt ttg
atg ttc atc agg] 3'
```

Each 50 μl polymerase chain reaction contained 0.3 μM of each primer (reaction (a) contained the pUC primers; reaction (b) contained the Adeno2 primers; and reaction (c) contained the SV40 primers), 1 μl AmpliTaq (Perkin Elmer Cetus), 1 ng of template DNA (SV40 cut with Kpn I; Adenovirus 2; or pUC19 cut with EcoRI (all DNAs from Life Technologies, Inc., Gaithersburg, Md.)) and 1×PCR buffer (50 mM KCl, 10 mM Tris HCl pH 8.3, 1.5 mM $MgCl_2$, 5 mM 2-mercaptoethanol). Cycling conditions were 94° 5 min; thirty cycles of 94° 30 sec, 55° 30 sec. 72° 2 min; and hold at 0°.

UDG cloning was used to clone the PCR products. One μl of each PCR product was combined with 14 μl water, 2 μl 10×PCR buffer, and 1 μl=1 unit UDG (Life Technologies, Inc., Gaithersburg, Md.), incubated 37° 30 min, and transformed 1 μl into DH5 alpha cells (Life Technologies, Inc., Gaithersburg, Md.). About 2500 colonies were obtained. Twelve colonies were picked for minipreps. Of these twelve, eleven gave the expected 6 Ssp I fragments of the expected size.

One of these plasmids was chosen and named "pML1". This plasmid is exactly 4700 bp, and contains six Ssp I (blunt) fragments, of sizes 2000, 1200, 800, 400, 200 and 100 bp.

Thus, when 470 ng of this complete digest are applied to a gel, the six fragments contain 200, 120, 80, 40, 20 and 10 ng of DNA.

EXAMPLE 2

Construction of a NotI Marker Ladder

A marker ladder can be constructed from PCR products. The sizes of the resulting DNAs can be selected by positioning the PCR primers appropriately. In addition, the incorporation of restriction sites in the primers, which are absent in the template molecules that are amplified during PCR, allows the ends of the PCR products to be cleaved with cognate restriction enzymes. If multiple PCR product DNAs are joined together and transformed into bacteria, and if one or more of the PCR products contains an origin of replication and a selection marker, the joined molecule can be recovered from the bacteria as a recombinant molecule. Digestion of the molecule with the restriction enzyme whose sites have been placed in the primers yields the desired fragments. By using a variety of restriction enzyme sites to link PCR products, and a different restriction enzyme to cleave the resulting recombinant plasmid, multiple DNAs can be joined together in a particular order to give the desired product.

Using these principles, a marker plasmid can be constructed as follows. Three PCR products are synthesized. Terminal restriction sites allow joining the fragments in a unique order and orientation. NotI sites will be used to release the three desired fragments from the resulting plasmid. Spacers at the ends of the PCR products ensure efficient restriction enzyme cutting.

```
         PCR product I, 2026 bp from pUC:

Nsp V    Not I
Left primer:    5 10 nt spacer/tt^cgaa/gc^ggccgg/
                   pUC19 coord. 637-656
                   taa tga atc ggc caa cgc gc 3

BssH I
Right primer:   5 10 nt spacer/g^cgcgc/
                   pUC 19 coord. 2622-2603
                   ga cgt cag gtg gca ctt ttc 3
```

```
         PCR product II, 1026 bp from SV40 DNA:

Mlu I    Not I
Left primer:    5 10 nt spacer/a^cgcgt/gc^ggccgc/ggt
                   SV40 coord. 108-129
                   tgc tga cta att gag atg c 3

BamH I
Right primer:   5 10 nt spacer/g^gatcc/
                   SV40 coord. 1093-1074
                   gtg agg tga gcc tag gaa tg 3
```

```
         PCR product III, 526 bp from adenovirus 2:

Bgl II   Not I
Left primer:    5' 10 nt spacer/a^gatct/gc^ggccgc/
                   Ad2 coord. 1022-1041
                   ggt ctt gtc att atc acc gg 3'

Cla I
Right primer:   5' 10 nt spacer/at^cgat/gtt
                   Ad2 coord. 1507-1488
                   gcc cag act cgt taa gc 3'
```

Each PCR product is digested with the two enzymes that cut at each end, i.e., I+Nsp V and BssH II, II with Mlu I and BamH I, and III with Bgl II and Cla I. The three digested products are mixed and joined, and the products are digested with the six restriction enzymes prior to transformation into E. coli. The amplified fragments must be chosen to lack internal sites for these enzymes. The only clones that should be produced by this process should be 3500 bp plasmids which can be cleaved with Not I to give three fragments of 2000, 1000, and 500 bp. Electrophoresis of 350 ng of this digest will give three bands containing 200, 100, and 50 ng DNA, respectively.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed is:

1. A nucleic acid marker kit comprising a carrier means having in close confinement therein at least one container means where the first container means contains a nucleic acid marker ladder comprising 3 or more nucleic acid fragments, wherein the size of each said fragment in base pairs is a multiple of an integer between 10 and 100, and wherein the mass of each said fragment is equal in its size in base pairs divided by the sum of the sizes in base pairs of all said fragments times the total mass of all said fragments.

2. The nucleic acid marker kit according to claim 1, wherein the nucleic acid marker ladder is dispersed in an aqueous carrier medium.

3. The nucleic acid marker kit according to claim 1, wherein the nucleic acid marker ladder comprises more than 4 nucleic acid fragments.

4. The nucleic acid marker kit according to claim 1, wherein the nucleic acid marker ladder comprises more than 10 nucleic acid fragments.

5. The nucleic acid marker kit according to claim 1, wherein the nucleic acid fragments are derived from one or more nucleic acid molecules by digestion with one or more restriction endonucleases.

6. The nucleic acid marker kit according to claim 1, wherein the integer is 10.

7. The nucleic acid marker kit according to claim 1, wherein the integer is 25.

8. The nucleic acid marker kit according to claim 1, wherein the integer is 50.

* * * * *

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 41 base pairs
      (B) TYPE: nucleic acid
      (C) STRANDEDNESS: single
      (D) TOPOLOGY: linear (xi) SEQUENCE DESCRIPTION: SEQ ID NO: 1:

AUCUGACCUC AUAATTTACG GAAGCATAAA GTGTAAAGCC T          41

(2) INFORMATION FOR SEQ ID NO: 2:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2:

```
AGUCACAGCU AUAATATTGG AAATGTGCGC GGAACCCC                           38
```

(2) INFORMATION FOR SEQ ID NO: 3:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 3:

```
AUAGCUGUGA CUAATTTACT AGTGAATCCA CAGAAACTAG C                      41
```

(2) INFORMATION FOR SEQ ID NO: 4:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 4:

```
ACAUCUGGAC UUAATATTAG ACATATTGAT AAGGTGGCGA G                      41
```

(2) INFORMATION FOR SEQ ID NO: 5:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 5:

```
AAGUCCAGAU GUAATTTAGG GACAGTTTGG CAAGGTTTTT A                      41
```

(2) INFORMATION FOR SEQ ID NO: 6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO: 6:

```
AUGAGGUCAG AUAATATTTA AGCCTTTTTG ATGTTCATCA GG                     42
```

(2) INFORMATION FOR SEQ ID NO: 7:

(i) SEQUENCE CHARACTERISTICS:
        (A) LENGTH: 34 base pairs
        (B) TYPE: nucleic acid
        (C) STRANDEDNESS: both
        (D) TOPOLOGY: both (xi) SEQUENCE DESCRIPTION: SEQ ID NO: 7:

```
TTCGAAGCGG CCGGTAATGA ATCGGCCAAC GCGC                              34
```

-continued

```
(2) INFORMATION FOR SEQ ID NO: 8:

(i) SEQUENCE CHARACTERISTICS:
        (A) LENGTH: 26 base pairs
        (B) TYPE: nucleic acid
        (C) STRANDEDNESS: both
        (D) TOPOLOGY: both (xi) SEQUENCE DESCRIPTION: SEQ ID NO: 8:

GCGCGCGACG TCAGGTGGCA CTTTTC                                        26

(2) INFORMATION FOR SEQ ID NO: 9:

(i) SEQUENCE CHARACTERISTICS:
        (A) LENGTH: 36 base pairs
        (B) TYPE: nucleic acid
        (C) STRANDEDNESS: both
        (D) TOPOLOGY: both (xi) SEQUENCE DESCRIPTION: SEQ ID NO: 9:

ACGCGTGCGG CCGCGGTTGC TGACTAATTG AGATGC                              36

(2) INFORMATION FOR SEQ ID NO: 10:

(i) SEQUENCE CHARACTERISTICS:
        (A) LENGTH: 26 base pairs
        (B) TYPE: nucleic acid
        (C) STRANDEDNESS: both
        (D) TOPOLOGY: both (xi) SEQUENCE DESCRIPTION: SEQ ID NO: 10:

GGATCCGTGA GGTGAGCCTA GGAATG                                        26

(2) INFORMATION FOR SEQ ID NO: 11:

(i) SEQUENCE CHARACTERISTICS:
        (A) LENGTH: 34 base pairs
        (B) TYPE: nucleic acid
        (C) STRANDEDNESS: both
        (D) TOPOLOGY: both (xi) SEQUENCE DESCRIPTION: SEQ ID NO: 11:

AGATCTGCGG CCGCGGTCTT GTCATTATCA CCGG                               34

(2) INFORMATION FOR SEQ ID NO: 12:

(i) SEQUENCE CHARACTERISTICS:
        (A) LENGTH: 26 base pairs
        (B) TYPE: nucleic acid
        (C) STRANDEDNESS: both
        (D) TOPOLOGY: both (xi) SEQUENCE DESCRIPTION: SEQ ID NO: 12:

ATCGATGTTG CCCAGACTCG TTAAGC                                        26
```